US00PP33919P2

(12) United States Plant Patent
Koot

(10) Patent No.: US PP33,919 P2
(45) Date of Patent: Feb. 1, 2022

(54) ***ACER* PLANT NAMED 'SONKOOT9'**

(50) Latin Name: *Acer palmatum*
Varietal Denomination: SONKOOT9

(71) Applicant: Johannes Adrianus Maria Koot, Kaatsheuvel (NL)

(72) Inventor: Johannes Adrianus Maria Koot, Kaatsheuvel (NL)

(73) Assignee: BOTANIC EXPERIENCE B.V., Kaatsheuvel (NL)

( * ) Notice: Subject to any disclaimer, the term of this patent is extended or adjusted under 35 U.S.C. 154(b) by 0 days.

(21) Appl. No.: 17/351,178

(22) Filed: Jun. 17, 2021

(51) Int. Cl.
*A01H 5/00* (2018.01)

(52) U.S. Cl.
USPC ..... Plt./224

(58) Field of Classification Search
USPC ..... Plt./224
See application file for complete search history.

*Primary Examiner* — Annette H Para
(74) *Attorney, Agent, or Firm* — Penny J. Aguirre

(57) ABSTRACT

A new cultivar of *Acer palmatum* tree named 'SONKOOT9' that is characterized by its broadly spreading upright plant habit, its leaves with laciniate leaf lobes (dissectum-like), its young leaves that are orange in color, and its summer foliage that is yellow to yellow green in color.

2 Drawing Sheets

Botanical classification: *Acer palmatum.*
Variety denomination: 'SONKOOT9'.

CROSS REFERENCE TO A RELATED APPLICATION

This application is related to a European plant breeders' rights application filed on Mar. 10, 2020, application No. 2020/0680. There have been no offers for sale anywhere in the world prior to the effective filing date of this Application and no accessibility to one of ordinary skill in the art could have been derived from the printed plant breeder's rights documents.

BACKGROUND OF THE INVENTION

The present invention relates to a new and distinct cultivar of *Acer palmatum* and will be referred to hereafter by its cultivar name, 'SONKOOT9'. 'SONKOOT9' is a deciduous tree grown for use as a landscape plant.

The new cultivar of *Acer* arose from a breeding program conducted by the Inventor in Kaatsheuvel, The Netherlands with the goal of developing an *Acer* cultivar with yellow or orange colored leaves that are dissectum-like. The new cultivar arose from a cross made in spring of 2012 between *Acer palmatum* cultivars 'Emerald Lace' (not patented) as the female parent and 'Orange Dream' (not patented) as the male parent. The Inventor selected 'SONKOOT9' as a single unique plant amongst the seedlings that resulted from the above cross in spring of 2016.

Asexual propagation of the new cultivar was first accomplished by stem cuttings by the Inventor in Kaatsheuvel, The Netherlands in late spring of 2016. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'SONKOOT9' as a new and unique cultivar of *Acer.*

1. 'SONKOOT9' exhibits a broadly spreading upright plant habit.
2. 'SONKOOT9' exhibits leaves with laciniate leaf lobes (dissectum-like).
3. 'SONKOOT9' exhibits young leaves that are orange in color.
4. 'SONKOOT9' exhibits summer foliage that is yellow to yellow green in color.

The female parent plant of 'SONKOOT9' differs from 'SONKOOT9' in having a dome-shaped plant habit that is considerably less upright and spring and summer foliage that is green in color. The male parent plant of 'SONKOOT9' differs in having a broadly upright plant habit and non-laciniate leaf lobes. 'SONKOOT9' can be compared to the *Acer* cultivars 'Seiryu' (not patented) and 'Aureum' (not patented). 'Seiryu' is similar to 'SONKOOT9' in having an upright plant shape and a similar leaf shape. 'Seiryu' differs from 'SONKOOT9' in having a taller plant height, a more upright plant habit, spring foliage that is yellow-green in color, and summer foliage that is green in color. 'Aureum' is similar to 'SONKOOT9' in having summer foliage that is yellow in color. 'Aureun' differs from 'SONKOOT9' in having a taller plant height, a more upright plant shape, non-laciniate leaf lobes, and spring foliage that is yellow in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date.

BRIEF DESCRIPTION OF THE DRAWINGS

The accompanying color photographs illustrate the overall appearance and distinct characteristics of the new cultivar as grown in Kaatsheuvel, The Netherlands.

Figure 1:
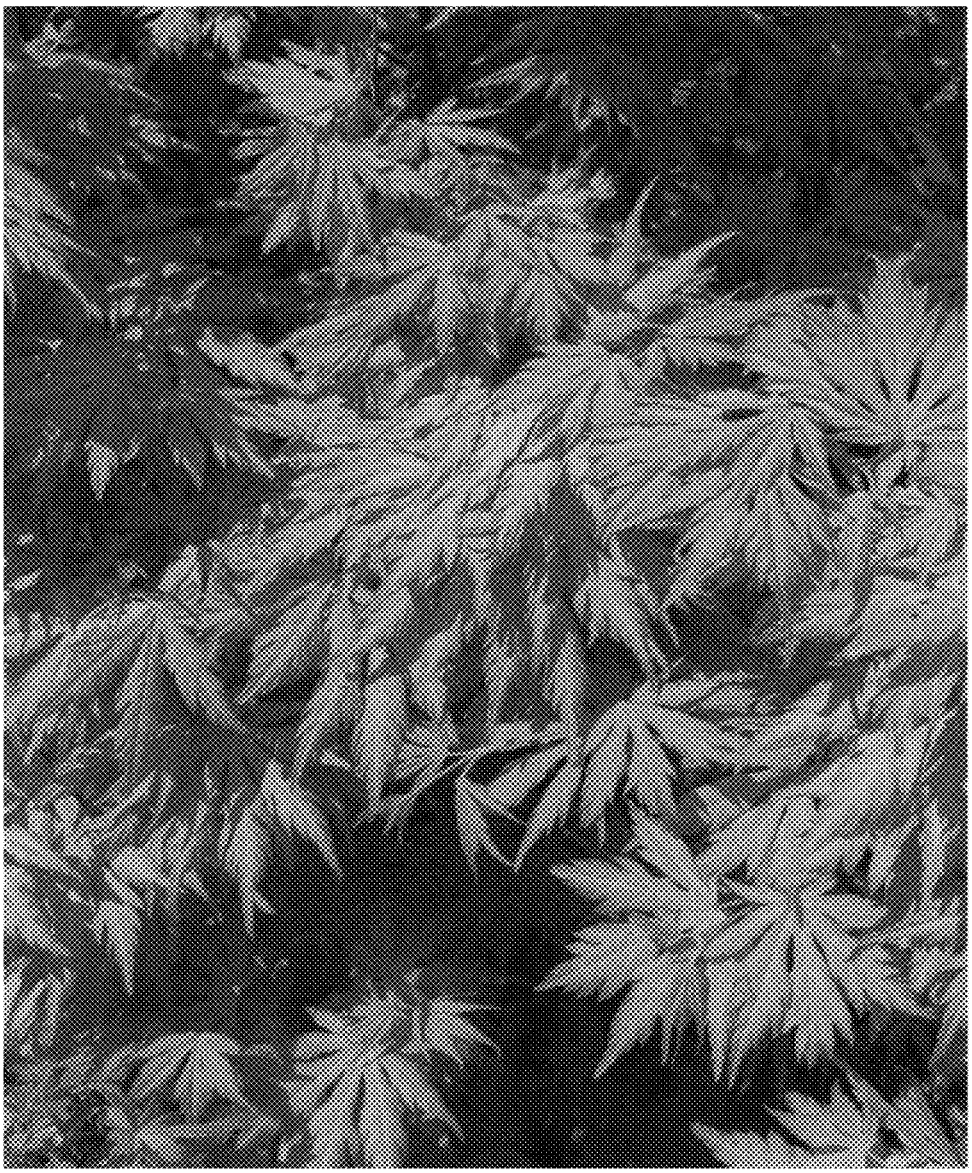
FIG. 1 provides a close-up view of the spring foliage of 'SONKOOT9' as a tree 5-years-in-age as grown outdoors.
Figure 2:
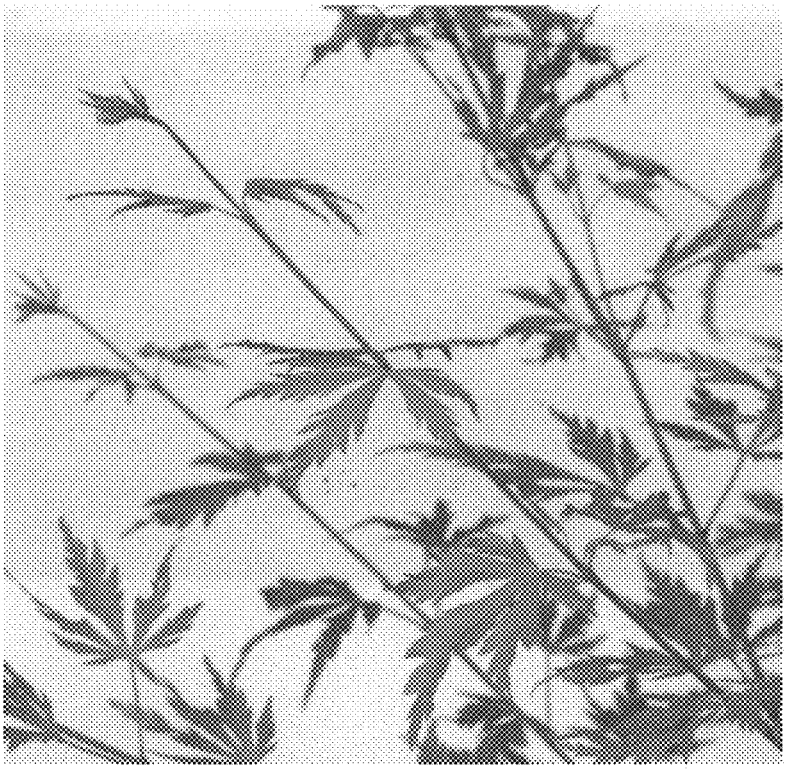

The photograph in FIG. 2 provides a close-up view of the semi-mature foliage of 'SONKOOT9' of a tree 13 months in age as grown in a conventional greenhouse in a 21-cm container.

Figure 3:
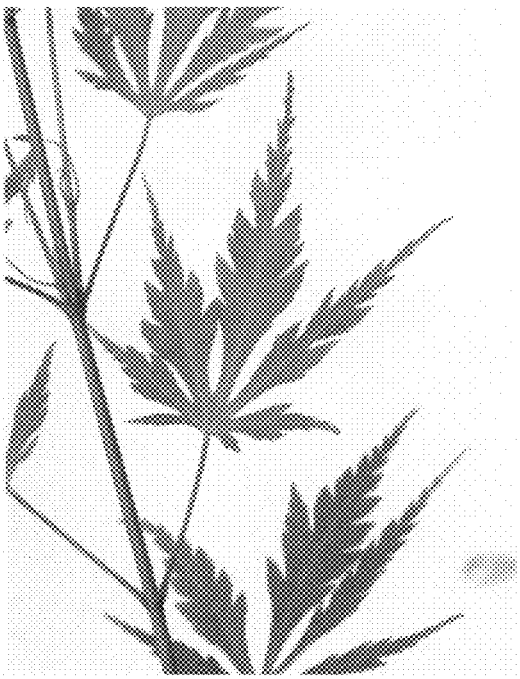

The photograph in FIG. 3 provides a close-up view of the mature leaves of 'SONKOOT9' as a tree 13 months in age as grown in a conventional greenhouse in a 21-cm container.

The colors in the photographs may differ slightly from the color values cited in the detailed botanical description, which accurately describe the colors of the new *Acer*.

DETAILED BOTANICAL DESCRIPTION

The following is a detailed description of 23-month-old trees of the new cultivar as grown in a greenhouse under ambient light in 21-cm containers in June in Kaatsheuvel, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type*.—Deciduous shrub.

*Plant habit*.—Broadly spreading and upright.

*Height and spread*.—An average of 69.5 cm in height and 84.5 cm in diameter as a 23-month old tree, reaches about 2 m in height and spread in the landscape.

*Cold hardiness*.—At least to U.S.D.A. Zone 6.

*Diseases and pests*.—No susceptibility or resistance to diseases or pest has been observed.

*Root description*.—Fibrous, freely branched.

*Propagation*.—Stem cuttings.

*Root development*.—Time required for root initiation is an average of 5 weeks, time required to produce a rooted cutting is an average of 6 months.

*Growth rate*.—Moderate to highly vigorous.

Branch description:

*Stem shape*.—Round.

*Stem size*.—An average of 52.7 cm in length, 2.75 mm in diameter.

*Stem surface*.—Slightly glossy.

*Stem color*.—Young; 161A, lower side 164A, mature; 164A, lower side a blend of 145A and 146D, internodes 146D, older stems; 147B and 147D.

*Stem strength*.—Strong.

*Stem aspect*.—An average angle of 47.5° to vertical.

*Internode length*.—An average of 5.7 cm.

*Branching*.—Very freely branching, 3 main branches and 23 secondary branches per main branches.

Foliage description:

*Leaf shape*.—Palmately, deeply lobed to cleft, broadly ovate to orbicular in outline.

*Leaf division*.—Simple.

*Leaf base*.—Hastate.

*Leaf apex*.—Narrow acute.

*Leaf fragrance*.—None.

*Leaf venation*.—Palmate, color; young upper surface 13B to 13C, young lower surface 170A, mature upper surface 145A, mature lower surface 146D.

*Leaf quantity*.—An average of 20 (10 pairs) per lateral branch.

*Leaf margins*.—Laciniate, biserrate, 5 lobes, sinus depth is very deep, sinus orientation is convergent.

*Leaf arrangement*.—Opposite.

*Leaf aspect*.—Flat, leaves in an average angle of 57.5° to lateral branch.

*Leaf attachment*.—Petiolate.

*Leaf surface*.—Texture of both surfaces glabrous and smooth, very slightly glossy, main veins of young leaves sparsely covered with a thin pubescence on both sides, an average of 0.3 mm in length, too small to measure.

*Leaf size*.—Average of 7.5 cm in length and width.

*Leaf color*.—Young leaves upper surface; 168B, 169C and 169D, fading in spring to 151C, narrowly margined 170A, young leaves lower surface; 151A, broadly margined 170A, later in spring fading to 151B to 151C, narrowly margined 170A, mature upper and lower surface 144B, fall upper and upper lower surface; 169A to 169D and 170A to 170B.

*Petioles*.—Average of 3.1 cm in length and 1 mm in diameter, both surfaces moderately glossy, strong, upper surface color; 181B, lower surface color; 150D and 160D.

*Stipules*.—None.

Inflorescence description: None produced to date.

Fruit and seed: None produced.

It is claimed:

1. A new and distinct cultivar of *Acer palmatum* tree named 'SONKOOT9' as herein illustrated and described.

* * * * *